United States Patent [19]

Peterson

[11] 4,129,516

[45] Dec. 12, 1978

[54] ENERGY SAVING DETERGENT MANUFACTURE

[75] Inventor: Donald J. Peterson, Cincinnati, Ohio

[73] Assignee: The Procter & Gamble Company, Cincinnati, Ohio

[21] Appl. No.: 731,182

[22] Filed: Oct. 12, 1976

[51] Int. Cl.$^2$ .......................... C11D 9/30; C11D 15/04
[52] U.S. Cl. .................................... 252/122; 252/108; 252/117; 252/141; 252/367; 252/41; 260/417; 260/426
[58] Field of Search ............... 252/367, 108, 117, 141, 252/122, 41, 369; 260/413–416, 417–418, 419, 426

[56] References Cited

U.S. PATENT DOCUMENTS 2,753,363  7/1956  Winer .............................. 260/417 X Primary Examiner—Mayer Weinblatt
Attorney, Agent, or Firm—Jerry J. Yetter; Julius P. Filcik; Richard C. Witte

[57] ABSTRACT

Soaps with low water content are prepared in an alkyl nitrile reaction medium and used to adjust the total water content of an aqueous crutcher mix to an intermediate moisture level without heat input.

18 Claims, No Drawings

ENERGY SAVING DETERGENT MANUFACTURE

BACKGROUND OF THE INVENTION

The present invention encompasses methods for preparing solid soap and detergent compositions. More specifically, fatty acid esters are saponified with an alkali metal hydroxide in a liquid reaction medium comprising an alkyl nitrile to provide alkali metal salt soaps of low moisture content. Soaps prepared in this manner are used to "dry" wet process soaps or synthetic detergent crutcher mixes to achieve an intermediate moisture level without the need for heat energy.

Traditional soap making processes are typically carried out using alkali metal bases, fatty acid esters, and water as the reaction medium. Heretofore, wet soap making processes have been energy intensive for at least two reasons. First, heat energy is required to initiate and sustain the saponification of the fatty acid esters by the aqueous solution of base. Second, the soaps are highly solvated by the water from the aqueous reaction medium. Accordingly, when preparing a granular, flaked or bar soap product, some water must be removed from the hydrated soap, and heat energy is used for this water removal step.

Likewise, in the preparation of solid detergent compositions comprising a synthetic detersive surfactant and optional detersive ingredients, the typical commercial process encompasses slurrying the detersive surfactant and other ingredients in an aqueous medium (crutcher mix) to provide homogeneity. The aqueous crutcher mix must then be dried, typically, spray-dried, to secure homogeneous detergent granules. Spray drying is also an energy intensive process.

From the foregoing, it will be readily appreciated that any means whereby the high water content of wet process soaps or aqueous crutcher mixes can be adjusted to some lower level without heat input would be advantageous. However, simply absorbing the water onto inert filler ingredients is not a desirable means for securing a lower moisture level, inasmuch as filler materials add nothing to the cleaning performance of the final compositions.

Soap, in a form having a low moisture content, or substantially dry, would be an excellent material for adjusting the moisture content of wet soaps or detergent crutcher mixes. However, low moisture content soaps prepared without an energy-intensive drying step have not been available heretofore.

The co-pending applications of Peterson, entitled SOAP MAKING, Ser. No. 731,183, filed Oct. 12, 1976, and HYDRATED SOAP MAKING, Ser. No. 731,163, filed Oct. 12, 1976, the disclosures of which are incorporated herein by reference, describe means for preparing substantially anhydrous and/or low moisture content soaps without the need for a heat drying step. Soaps prepared by the Peterson process are used in the present invention as the drying agent for wet process soaps and aqueous crutcher mixes.

The co-pending application of Peterson, entitled BASE REACTANT, Ser. No. 731,176, filed Oct. 12, 1976, discloses and claims a composition of matter which comprises an alkyl nitrile and an alkali metal hydroxide, as used in the Peterson soap making process.

RELATED REFERENCES

The art of preparing the alkali metal salts of organic acids, especially as it is embodied in soap making processes, is old and is the subject of a large body of literature. Anhydrous soap making processes have been disclosed heretofore, as have soap making processes which employ organic solvents as the reaction medium. The alkyl nitriles used as the reaction medium in the present process are well-known materials.

Despite the voluminous literature in this area and the long history of soap making and syntheses of fatty acid salts, the present process does not appear to have been contemplated heretofore.

Acetonitrile (methyl cyanide; cyanomethane; ethanenitrile) is a highly preferred alkyl nitrile solvent for use in the present process. As pointed out in THE MERCK INDEX, Seventh Ed., page 8, this material has been used to extract fatty acids from fish liver oils and other animal and vegetable oils. This material is also known as a medium for producing reactions involving ionization, as a solvent in non-aqueous titrations, and as a non-aqueous solvent for inorganic salts.

The use of acetonitrile as an extraction solvent for separating/removing various materials from compositions containing fatty acids, sterols, and the like, is disclosed in the following references: U.S. Pat. Nos. 2,681,922, Balthis, 6/22/54; 2,528,025, Whyte, 10/31/50; Chemical Abstracts 38 6180; 84 80436u; 48 6698; 57 13224; 47 3660; 60 2330; 49 15266; 54 5126; 50 14322; and 46 6468.

The use of propionitrile in various liquid phase extraction processes involving glycerides, fatty acids, and the like, is disclosed in U.S. Pat. Nos. 2,316,512, Freeman, 4/13/43; 2,200,391, Freeman, 5/14/40; 2,313,636, Freeman, 3/9/43; 2,390,528, Freeman, 12/11/45; and Canadian Pat. No. 488,250, Freeman, 11/18/52.

Processes for manufacturing modified oil products from fatty oils, for manufacturing soap compositions, and for preparing metallic salts of higher fatty acids, which are carried out under anhydrous conditions or with the use of organic solvents of various types are disclosed in the following references: U.S. Pat. Nos. 1,957,437, Auer, 5/8/34; 3,376,327, Freeland, 4/2/68; 2,271,406, Thurman, 1/27/42; 2,383,630, Trent, 8/28/45; 3,476,786, Lally and Cunder, 11/4/69; Chemical Abstracts 53 20838; 26 5875; 52 7743; and 53 20850.

Various miscellaneous references relating to the use of cyano compounds or amines of various types in the preparation of carboxylic acids and general references to the use of acetonitrile as a solvent are as follows; U.S. Pat. Nos. 2,042,729, Ralston and Poole, 6/2/36; 3,828,086, Kenney and Donahue, 8/6/74; 3,519,657, Olah, 7/7/70; 2,211,941, Sullivan, 8/20/40; 1,833,900, Hoyt, 12/1/31; 2,402,566, Milas, 6/25/46; 2,640,823, Gloyer and Vogel, 6/2/53; 2,895,974, Case, 7/21/59; and Chemical Abstracts 53 9642.

German Patentschrift No. 1,254,139, May 30, 1968, discloses a process for preparing saturated fatty acids by reacting an α-olefin with a stoichiometric excess of acetonitrile, or acetate reagent, in the presence of an organic peroxide.

It is clear that the use of the alkyl nitriles as an extraction/separation medium in the manner suggested by these references does not contemplate their use as a reaction solvent in the manner of the present invention. Moreover, the use of organic solvents, anhydrous conditions, or cyano compounds to prepare soaps, and the like, does not contemplate the present invention.

Attention is specifically directed to U.S. Pat. No. 3,133,942, Hahl, patented May 19, 1964, and U.S. Pat.

No. 2,753,364, Boner and Breed, patented July 3, 1956. The U.S. Pat. No. 3,133,942 relates to the production of metal salts of organic acids and, as disclosed therein, is carried out by using an organic acid and certain metals in the form of metal powders. Inert organic solvents, including acetonitrile, propionitrile and benzonitrile, are disclosed for use in the process. The process differs from that of the present invention in that it uses neither alkali metal hydroxides nor organic acid esters as the starting materials. Moreover, many of the solvents disclosed as being useful in the U.S. Pat. No. 3,133,942 are not contemplated for use herein.

The Boner, et al., patent, above, relates to a method for manufacturing lithium soaps (lubricating greases) using lithium carbonate and free fatty acids as the starting materials. Acetonitrile, benzonitrile and "benzyl cyanide" are taught to be useful solvents in the process, along with many other organic solvents. It will be appreciated that this reference does not teach the use of alkali metal hydroxides, nor organic esters, especially glyceride esters, such as those used in the present invention; is almost unlimited as to the type of organic nitrogen-containing materials suggested for use as the solvent medium; and does not teach or suggest the present process which is limited to the alkyl nitriles which have now been discovered to be particularly advantageous when employed in the manner disclosed herein.

Attention is also directed to the review article *Khim. Prom.* (Moscow) 1968 44 (10) 722–6 (Russ.) which, in abstract form (C.A. 70 28299y), is said to relate to the use of MeCN as a solvent, its reactions with aldehydes, ketones, alcohols, dienes and organic acids, substitution reactions and with inorganic compounds, and which cites 90 references.

Attention is also directed to the review article by E. J. Fischer, *Allgem. Oel-u. Fett-Ztg.* 33, 78–81 (1936) which, in abstract form (C.A. 30 3539), is said to relate to methods for preparing acetonitrile and its use, principally as a solvent.

The foregoing references do not appear to contemplate the preparation of soaps by the Peterson process, nor do they suggest the use of the Peterson process soaps as drying agents in the manner of this invention.

SUMMARY OF THE INVENTION

The present invention encompasses a process for adjusting the water content of wet soaps or wet crutcher mixes to a lower total water content by the addition of soap which has a low water content. The low water content soap used as the "drying agent" in this process is prepared in an energy-sparing manner, and has not been available, heretofore.

The soap used as the drying agent in the present process is prepared according to the Peterson process, referred to above, and comprises saponifying fatty acid esters with an alkali metal hydroxide in a reaction medium comprising an alkyl nitrile. Glyceride esters, including the mixed mono-, di- and triglyceride esters derived from animal fats and oils and/or vegetable fats and oils can be used in the Peterson process. Such materials typically comprise fatty acid ($C_{10}$–$C_{20}$) esters, are well known for use in soap making processes, and yield the alkali metal salts of $C_{10}$–$C_{20}$ organic acids in any degree of hydration desired, including substantially anhydrous soaps, without a heat drying step.

The Peterson process is simply and economically carried out by admixing the alkyl nitrile reaction medium, the ester, and the alkali metal hydroxide in a suitable container, initiating the reaction (typically, by gentle heating) and allowing the reaction to proceed to completion.

Soaps prepared in the foregoing manner simply precipitate from the reaction medium as an unsolvated, substantially white powder. Controlled amounts of water can optionally be present during the Peterson process, while still providing solid, filterable soaps of controlled degrees of hydration. Advantageously, much of the colored matter which is commonly present in commercial grades of animal fats and oils used as the ester starting material is retained in solution in the alkyl nitrile. Accordingly, an excellent soap product, substantially free from color bodies, can be secured by the Peterson process for use in the present invention. Typical yields of anhydrous and/or low moisture content solid soaps prepared by the Peterson process are in the range of 90% in a matter of a few minutes, without an energy intensive drying step. These Peterson process soaps are used in the practice of this invention.

DETAILED DESCRIPTION OF THE INVENTION

The present invention encompasses an energy-saving process for adjusting the water content of wet soaps, wet non-soap detersive surfactants, or wet crutcher mixes to a lower total water content by adding to said wet materials a quantity of a drying agent which comprises a soap having a low water content which is prepared by saponifying fatty acid esters with alkali metal hydroxides in a reaction medium which comprises an alkyl nitrile. The preparation of the drying agent soap is, as indicated, carried out by the Peterson process, which involves the saponification of organic acid esters with alkali metal hydroxides in an alkyl nitrile reaction medium. The Peterson process does not appear to depend on the nature of the acid ester used; hence, the organic acid esters employed in the Peterson process can be simple alkyl or aryl esters, or can be glyceride esters such as the triglycerides which typically constitute the major proportion of the materials present in fats and oils derived from animal or vegetable sources. Accordingly, the Peterson process can be used to prepare water-soluble soaps, i.e., the alkali metal salts of $C_{10}$–$C_{20}$ fatty acids, by saponifying esters of organic acids having chain lengths in that range. Alkali metal salts of organic acids having chain lengths longer or shorter than that mentioned above, as well as branched chain and aryl organic acids, are also available in a substantially dry or low moisture content form via the Peterson process and can also be employed as a drying agent herein, if desired. Most preferably, however, the alkali metal salts of the $C_{10}$–$C_{20}$ fatty acids are used as the drying agent soaps in the practice of this invention since these materials have substantial detersive properties in the final compositions prepared by the present process.

By "soaps" herein is meant the alkali metal salts of organic acids of the formula RCOOM, wherein the RCOO-group is an organic acid substituent having a total carbon content in the range of $C_{10}$–$C_{20}$, and wherein M is an alkali metal.

By "wet soaps" herein is meant tacky, viscous, water-soluble soap materials, generally characterized by a water content greater than about 14%, by weight.

By "wet crutcher mix" herein is meant an aqueous slurry or solution of detersive ingredients which is characterized by a water content greater than about 14%, by weight, and which will ultimately be dried to a solid, homogeneous detergent (or soap) composition.

By "soap having a low water content" herein is meant a water-soluble, solid soap material having a water content in the range of from about 0% to about 14%, by weight, and made by the Peterson process. Such soaps are used as the drying agent in the practice of the present invention.

By "fatty acid esters" herein is meant a compound of the formula RCOOR', wherein RCOO— is as above, and wherein group R' is an organic substituent group derived from an alcohol or polyol, unlimited in type.

By "alkali metal hydroxide" herein is meant lithium hydroxide, sodium hydroxide, potassium hydroxide, rubidium hydroxide and cesium hydroxide. Sodium hydroxide and potassium hydroxide are especially useful for making water-soluble soaps for detergent use.

By "alkyl nitrile" herein is meant a compound of the formula R"CN, wherein R" is a linear, branched chain or cyclic aliphatic substituent. Typical examples of such materials are acetonitrile and propionitrile, which are preferred for use in the Peterson process for preparing the drying agent soaps used herein. Aromatic nitriles, e.g., benzonitrile, have been found not to be useful as a reaction medium in the Peterson process and are not encompassed by the present invention. Acetonitrile is the most highly preferred alkyl nitrile for preparing the drying agent soaps.

By "substantially water-free" herein is meant that water is not intentionally added to the alkyl nitrile reaction medium. Some water may be present in the reaction medium, inadvertently, but this usually only constitutes a small percentage in the reaction medium.

By "glycerides" herein is meant organic acid esters of glycerol. The term "glycerides" encompasses mono-, di- and triglycerides, since glycerol is a trihydric alcohol which can be esterified on any, or all, of the three hydroxyl groups. Triglycerides constitute the major components of naturally-occurring fats and oils which are typically used as starting materials in soap making processes, and can also be used as an economical raw material for making drying agent soaps by the Peterson process.

By "animal or vegetable fats and oils" herein is meant the organic acid glyceride materials which can be secured from a wide variety of sources. Specific, nonlimiting examples of such materials include lard, tallow, coconut oil, palm oil, various by-products from animal rendering operations, oils from oleaginous seeds such as the soybean, sunflower seeds, and the like, cottonseed oil, etc. Typical listings of such materials are widely available, and all such glyceride mixtures are useful in the present process.

By "wet non-soap detersive surfactant" herein is meant water-soluble, organic surface active agents other than carboxylate soaps having a water content of greater than about 14%, by weight. Such materials specifically include anionic, nonionic, zwitterionic, amphoteric and cationic detersive surfactants well known in the detergency arts. Typically examples of such materials are fully disclosed in U.S. Pat. Nos. 3,723,322; 3,597,416; and 3,213,030, to F. L. Diehl, the disclosures of which are incorporated herein by reference. The sulfated and/or sulfonated detersive surfactants, such as the alkyl benzene sulfates and sulfonates, are preferred non-soap detersive surfactants used herein in aqueous crutcher mixes to prepare spray-dried detergent granules.

By "auxiliary detersive agents" herein is meant well-known materials (other than detersive surfactants) such as water softeners, bleaches, soil suspending agents, anti-redeposition agents, and the like, commonly used in fully formulated, commercial detergent compositions. One type of preferred auxiliary detersive agent includes the detergency builder materials well known in the art. Typical examples of detergency builders are disclosed in many U.S. patents, including those of Diehl, above.

All percentages herein are by weight, unless otherwise specified.

Solid soaps prepared by the Peterson process and characterized by a low water content are used as drying agents in the practice of this invention. The Peterson process used to prepare the drying agent soaps for use herein is carried out by simply admixing the carboxylic acid ester to be saponified with the alkyl nitrile and the alkali metal hydroxide in any suitable reaction vessel. The reaction can be initiated by gently heating the mixture, if desired. However, the Peterson saponification reaction will generally initiate spontaneously on stirring of the reactants for a few minutes.

When preparing substantially anhydrous drying agent soaps by the Peterson process, a substantially water-free reaction medium is used. When preparing drying agent soaps having limited water content (i.e., water content of about 14%, and less) a concentrated, aqueous solution of LiOH or NaOH can be used in the Peterson process.

The Peterson process for preparing substantially anhydrous soaps employs solid alkali metal hydroxides, alkyl nitriles, and $C_{10}-C_{20}$ fatty acid esters. It is to be understood that the mixture of alkali metal hydroxide and alkyl nitrile is heterogeneous, since the hydroxides are not particularly soluble in the nitriles. Apparently, some alkali metal hydroxide does dissolve in the alkyl nitrile and saponifies an equivalent amount of the organic acid ester, whereupon additional alkali metal hydroxide dissolves, etc. For this reason, it is preferred to use alkali metal hydroxides which have been ground to an appropriate particle size to aid in dissolution in the alkyl nitrile. This is not critical to the Peterson process, but only makes the reaction more convenient. For general purposes, the alkali metal hydroxide can be ground to a particle size that passes through a 50 mesh sieve and used herein.

As noted above, the Peterson process can also be carried out using concentrated aqueous solutions of sodium hydroxide (preferred) or lithium hydroxide in combination with the alkyl nitrile and ester. Solid, white, filterable soap powders having a water content of 14%, or less, are still secured. However, aqueous solutions of KOH, RbOH or CsOH cannot be used, since the resulting soaps are highly hydrated, tacky, semi-solids which are not useful as drying agent soaps in the manner of this invention. One advantage of using concentrated solutions of NaOH in the Peterson process is that such solutions are more economical than the dry powdered alkali metal hydroxides.

The nature of the fatty acid esters employed in the Peterson soap making process is not critical, except that esters which yield fatty acids in the soap ($C_{10}-C_{20}$, especially $C_{12}-C_{18}$) chain length range are preferred.

In the Peterson process, it is convenient to employ a stoichiometric amount of the alkali metal hydroxide and ester to be saponified. For most purposes, an excess of the alkali metal hydroxide is employed to ensure that the reaction is carried to completion and that no ester is wasted. The alkyl nitrile is generally used in a solvent amount, i.e., sufficient to dissolve the acid ester. In some instances, the acid ester may not be entirely soluble in the alkyl nitrile and a ternary, heterogeneous reaction mixture of alkali metal hydroxide/alkyl nitrile/acid ester, or concentrated aqueous alkali metal hydroxide solution/alkyl nitrile/acid ester, is formed. It does not appear to be necessary for the reacton mixture to be homogeneous, and excellent yields of drying agent soaps for use herein are secured by the Peterson process even under such conditions.

In an alternate mode, an excess of ester is used, and the mixture of any unreacted ester and alkyl nitrile is simply re-used with fresh metal hydroxide solutions in subsequent processes. This avoids the need for any acid neutralization step to remove excess base during soap recovery.

The Peterson soaps are recovered as free-flowing solids by filtration. Any entrained alkyl nitrile can be removed by air drying.

Peterson soaps are conveniently prepared using weight ratios of ester:alkyl nitrile:alkali metal hydroxide in the range of from about 1:0.1:1 to about 1:1:5, but other ratios can be used, as desired.

Detersive Surfactants

Typical anionic detersive surfactants which can be employed herein include water-soluble sulfates or sulfonates of the general formula $R'''X^-Q^+$ wherein $R'''$ is an alkyl (including unsaturated alkyl), alkyl benzene or ethoxylated alkyl group, X is sulfate or sulfonate, and wherein Q is a counterion such as $H^+$, or a cationic moiety chosen such that the anionic surfactant is water-soluble, e.g., alkali metals, ammonium, alkanolammonium, and the like. It will be recognized that such anionic surfactants include the typical alkyl benzene sulfates and sulfonates, alkyl sulfates and sulfonates, and ethoxylated alkyl ether sulfates and sulfonates well known in the detergency arts. Such anionic surfactants are readily available from a variety of well-known commercial processes and sources.

More particularly, the anionic surfactants employed herein can be any of the water-soluble detersive materials of the type disclosed above. Mixtures of the foregoing anionic surfactants can also be employed herein. The preferred anionic surfactants herein include the $C_{10}$–$C_{18}$ alkyl benzene sulfates; $C_{10}$–$C_{18}$ alkyl benzene sulfonates; $C_{10}$–$C_{18}$ alkyl sulfates; $C_{10}$–$C_{18}$ alkyl sulfonates; ethoxylated $C_{10}$–$C_{18}$ alkyl ether sulfates; and ethoxylated $C_{10}$–$C_{18}$ alkyl ether sulfonates.

Highly preferred anionic surfactants employed herein by virtue of their superior detergency performance are the $C_{12}$–$C_{18}$ alkyl benzene sulfonates; the $C_{14}$–$C_{18}$ alkyl sulfates; and the $C_{12}$–$C_{18}$ ethoxylated alkyl ether sulfates.

Anionic surfactants can be employed herein in their free acid form. However, inasmuch as detergency performance in an aqueous liquor is usually substantially higher at basic pH's, the anionic surfactants are generally used in the form of their water-soluble salts. As noted hereinabove, any counterion which provides a water-soluble salt of the anionic surfactant is suitable for use, but the surfactants are most commonly and preferably used in their sodium salt form, for reasons of economy.

The following is a listing of anionic surfactants which are representative of those which can be employed in the present invention, but is not intended to be limiting thereof.

The alkyl benzene sulfate and sulfonate surfactants employed herein can be, for example, sodium dodecylbenzene sulfate; potassium dodecylbenzene sulfonate; sodium tetradecylbenzene sulfate; triethanolammonium tetradecylbenzene sulfonate; ammonium hexadecylbenzene sulfate; ammonium hexadecylbenzene sulfonate; diethanolammonium octadecylbenzene sulfonate; and monoethanolammonium octadecylbenzene sulfonate. In the alkyl benzene-based anionic surfactants, the alkyl group can either be in straight chain or branched chain configuration; the straight chain configuration is preferred, inasmuch as these compounds are biodegradable.

It will be recognized that, on a commercial scale, the alkyl benzene sulfates and sulfonates are readily prepared from petroleum fractions comprising mixtures of alkyl benzene feedstocks containing various chain length alkyl substituents. Alkyl benzene sulfates and sulfonates prepared from such mixed feedstocks are entirely suitable for use herein, and are preferred for economic reasons. The most highly preferred commercial mixtures of the alkyl benzene-based anionic surfactants are those containing major proportions of the "heavy" or long-chain alkyl materials. An especially preferred anionic mixture comprises the alkyl benzene sulfonates containing an average of about 11.8 carbon atoms in linear configuration in the alkyl group (abbreviated $C_{11.8}$ LAS).

The alkyl sulfate detersive surfactants employed herein are materials which are available from petrochemical and alcohol-based feedstocks. Specific examples of the alkyl sulfates and sulfonates useful herein include decyl sulfate; decyl sulfonate; dodecyl sulfate; dodecyl sulfonate; tetradecyl sulfate; tetradecyl sulfonate; hexadecyl sulfate; hexadecyl sulfonate; octadecyl sulfate; and octadecyl sulfonate. The most highly preferred alkyl sulfates and alkyl sulfonates are those wherein the alkyl chain length is from about $C_{14}$ to about $C_{18}$.

As in the case of the alkyl benzene-based anionic surfactants, the alkyl sulfates and sulfonates are most commonly employed in the form of water-soluble salts, with the sodium salt being the most preferred. Specific examples of preferred alkyl sulfates and sulfonates include sodium tetradecyl sulfate; ammonium tetradecyl sulfate; sodium hexadecyl sulfate; triethanolammonium hexadecyl sulfonate; monoethanolammonium octadecyl sulfate; triethanolammonium octadecyl sulfate; and sodium octadecyl sulfate.

As with the alkyl benzene-based anionic surfactants, mixtures of the alkyl sulfates and sulfonates can also be employed herein. Again, it is preferred that such mixtures contain major proportions of the long-chain, i.e., $C_{14}$ and greater, alkyl substituents, inasmuch as such compounds are better detergents than their shorter-chain homologs.

Mixed alkyl sulfates, especially those which can be prepared from the mixed fatty alcohols commonly known as coconut fatty alcohols and tallow fatty alcohols, are especially preferred for economic reasons. A highly preferred detersive alkyl sulfate mixture comprises the so-called tallow alkyl sulfates, and these contain more of the longer-chain alkyl materials than does the coconut-range fraction.

A third type of typical detersive anionic surfactant useful in the present invention encompasses the ethoxylated alkyl ether sulfates and sulfonates. Typically, such materials comprise a $C_{10}$–$C_{18}$ alkyl group which is ethoxylated with from 1 to about 20, more preferably 3 to about 10, ethoxyl groups, which are subsequently sulfated or sulfonated at the terminal position of the molecule. As with the alkyl sulfates, such ethoxylated materials can be mixtures resulting from the use of mixed alkyl feedstocks such as the coconut alcohols or tallow-based alcohols.

The ethoxylated alkyl ether anionic surfactants are typically employed in their salt form, with the sodium salt being preferred for economic reasons.

Representative, non-limiting examples of the ethoxylated alkyl ether surfactants employed herein are noted below. Following common practice, the degree of ethoxylation (EO) is indicated by the subscript notation. It is to be recognized that, in commercial practice, the degree of ethoxylation is commonly represented as an average of a given ethoxylated mixture. Sodium dodecyl $(EO)_3$ sulfate; potassium hexadecyl $(EO)_6$ sulfate; triethanolammonium octadecyl $(EO)_9$ sulfate; sodium decyl $(EO)_3$ sulfonate; and diethanolammonium octadecyl $(EO)_{12}$ sulfonate are all useful as the anionic surfactant of the present invention.

Mixed ethoxylated alkyl sulfates, such as sodium coconutalkyl $(EO)_6$ sulfate and sodium tallowalkyl $(EO)_9$ sulfate; are particularly useful detersive surfactants, inasmuch as these materials are commercially available and contain substantial portions of the higher ($C_{14}$ and greater) optimally detersive alkyl ether sulfates.

Nonionic detersive surfactants employed in the present invention are, typically, condensation products of relatively long-chain ethylene oxide moieties with primary alcohols, secondary alcohols, or alkyl phenols. Such nonionic surfactants are well known in the detergency art.

More specifically, nonionic detersive surfactants of the formula $R'''(EO)_x$, wherein: $R'''$ is a straight- or branched-chain hydrocarbyl moiety derived from a primary or secondary alcohol containing from about 8 to about 20, more preferably from about 10 to about 18, carbon atoms, or an alkyl phenol-based moiety wherein the alkyl chain is straight or branched and contains from about 6 to about 12 carbon atoms; EO is the standard abbreviation for the ethylene oxide moiety; and wherein subscript x denotes the degree of polymerization of the ethylene oxide moiety and is an integer in the range from about 1 to about 20, preferably 3 to about 9, can be used herein.

Specific, non-limiting examples of such nonionic surfactants include the following: n-$C_{10}(EO)_3$, n-$C_{12}(EO)_9$, n-$C_{14}(EO)_{12}$, n-$C_{10}(EO)_{15}$, n-$C_{12}(EO)_{20}$, n-$C_{12}(EO)_3$, sec-$C_{10}(EO)_9$, sec-$C_{12}(EO)_{12}$, sec-$C_{14}(EO)_{20}$, sec-$C_{10}(EO)_3$, decyl benzene $(EO)_9$, dodecyl benzene $(EO)_{15}$, tetradecyl benzene $(EO)_{20}$, and the like.

The foregoing pure nonionic detersive surfactants, and mixtures thereof, are all useful herein. However, it will be recognized that such pure materials are relatively expensive to prepare, in that they involve separation of pure alcohol or alkyl benzene phenol precursors, followed by ethoxylation and a second separation procedure to secure the pure compounds. For economic reasons, therefore, it is more preferred to use commercial mixtures of such materials.

Examples of commercial nonionic detersive surfactants herein include: Dobanol 91-8; Dobanol 91-12; Neodol 01 $E_{12}$ ($C_{10–11}$ alcohol avg. 12 EO groups), and the Kyro ethoxylates.

Zwitterionic and amphoteric detersive surfactants useful herein include the alkyl and alkaryl ammonium and sulfonium propane sulfonates known in the detergency arts.

Wet soaps, i.e., water-soluble detersive soaps having a moisture content of greater than about 14%, can also be used in the practice of this invention. Wet soaps are typically prepared by saponifying glycerides with alkali metal hydroxides in aqueous media. Wet soaps are efficiently dried by combining them with Peterson process soaps in the manner of this invention. The final soap composition thus prepared is in a phase which is suitable for compacting into bars, or can be used in free-flowing powder or flake form.

Auxiliary Detersive Agents

Crutcher mixes employed in the present process can optionally contain all manner of detergency builders commonly taught for use in both soap and non-soap detergent compositions. The compositions prepared in the present manner typically contain from about 0% to about 70% by weight, preferably from about 25% to about 65% by weight, of said builders. Useful builders herein include any of the conventional inorganic and organic water-soluble builder salts, as well as various water-insoluble and so-called "seeded" builders.

Inorganic detergency builders useful herein include, for example, water-soluble salts of phosphates, pyrophosphates, orthophosphates, polyphosphates, phosphonates, carbonates, polyhydroxysulfonates, silicates, polyacetates, carboxylates, polycarboxylates, and succinates. Specific examples of inorganic phosphate builders include sodium and potassium tripolyphosphates, phosphates, and hexametaphosphates. The polyphosphonates specifically include, for example, the sodium and potassium salts of ethylene diphosphonic acid, the sodium and potassium salts of ethane-1-hydroxy-1,1-diphosphonic acid and the sodium and potassium salts of ethane-1,1,2-triphosphonic acid. Examples of these and other phosphorus builder compounds are disclosed in U.S. Pat. Nos. 3,159,581; 3,213,030; 3,422,021; 3,422,137; 3,400,176 and 3,400,148, incorporated herein by reference. Sodium tripolyphosphate is an especially preferred, water-soluble inorganic builder herein.

Non-phosphorus containing sequestrants can also be selected for use herein as detergency builders.

Specific examples of non-phosphorus, inorganic builder ingredients include water-soluble inorganic carbonate, bicarbonate, and silicate salts. The alkali metal, e.g., sodium and potassium, carbonates, bicarbonates, and silicates are particularly useful herein.

Water-soluble, organic builders are also useful herein. For example, the alkali metal, ammonium and substituted ammonium polyacetates, carboxylates, polycarboxylates and polyhydroxysulfonates are useful builders in the present compositions and processes. Specific examples of the polyacetate and polycarboxylate builder salts include sodium, potassium, lithium, ammonium and substituted ammonium salts of ethylenediaminetetraacetic acid, nitrilotriacetic acid, oxydisuccinic acid, mellitic acid, benzene polycarboxylic acids, and citric acid.

Highly preferred non-phosphorus builder materials (both organic and inorganic) herein include sodium carbonate, sodium bicarbonate, sodium silicate, sodium citrate, sodium oxydisuccinate, sodium mellitate, sodium nitrilotriacetate, and sodium ethylenediaminetetraacetate, and mixtures thereof.

Other highly preferred organic builders herein are the polycarboxylate builders set forth in U.S. Pat. No. 3,308,067, Diehl, incorporated herein by reference. Examples of such materials include the water-soluble salts of homo- and co-polymers of aliphatic carboxylic acids such as maleic acid, itaconic acid, mesaconic acid, fumaric acid, aconitic acid, citraconic acid and methylenemalonic acid.

Additional, preferred builders herein include the water-soluble salts, especially the sodium and potassium salts, of carboxymethyloxymalonate, carboxymethyloxysuccinate, cis-cyclohexanehexacarboxylate, cis-cyclopentanetetracarboxylate and phloroglucinol trisulfonate.

Sodium nitrilotriacetate is an especially preferred, water-soluble organic builder herein.

Another type of detergency builder material useful in the present compositions and processes comprises a water-soluble material capable of forming a water-insoluble reaction product with water hardness cations in combination with a crystallization seed which is capable of providing growth sites for said reaction product. Such "seeded builder" compositions are fully disclosed in the U.S. patent application of Benjamin, Ser. No. 248,546, filed Apr. 28, 1972, the disclosures of which are incorporated herein by reference.

More particularly, the seeded builders useful herein comprise a crystallization seed having a maximum particle dimension of less than 20 microns, preferably a particle diameter of from about 0.01 micron to about 5 microns, in combination with a material capable of forming a water-insoluble reaction product with free metal ions.

Many builder materials, e.g., the water-soluble carbonate salts, precipitate water hardness cations, thereby performing a builder function. Unfortunately, many of the precipitating builers used in detergent compositions do not reduce the free metal ion content of laundry baths quickly, and such builders only compete with the organic detergent and the soil for the free metal ions. The result is that while some of the free metal ions are removed from the solution, some ions do react with the organic detergent and the soil, thereby decreasing the detersive action. The use of the crystallization seed quickens the rate of precipitation of the metal hardness, thereby removing the hardness ions before they can adversely affect the detergency performance.

By using a material capable of forming a water-insoluble product with free metal ions in combination with a crystallization seed, the combined free metal ion concentration of an aqueous laundering liquor can be reduced to less than 0.5 grains of hardness within about 120 seconds. The preferred seeded builders can reduce the free metal hardness of less than 0.1 grains/gallon within about 30 seconds.

Preferred seeded builders consist of: a water-soluble material capable of forming a reaction product having a solubility in water of less than about $1.4 \times 10^{-2}$ wt.% (at 25° C.) with divalent and polyvalent metal ions such as calcium, magnesium and iron; and a crystallization seed (0.001–20 micron diameter) which comprises a material which will not completely dissolve in water within 120 seconds at 25° C.

Specific examples of materials capable of forming the water-insoluble reaction product include the water-soluble salts of carbonates, bicarbonates, sesquicarbonates, silicates, aluminates and oxalates. The alkali metal, especially sodium, salts of the foregoing materials are preferred for convenience and economy.

The crystallization seed employed in such seeded builders is preferably selected from the group consisting of calcium carbonate; calcium and magnesium oxalates; barium sulfate; calcium, magnesium and aluminum silicates; calcium and magnesium oxides; calcium and magnesium salts of fatty acids having 12 to 22 carbon atoms; calcium and magnesium hydroxides; calcium fluoride; and barium carbonate. Specific examples of such seeded builder mixtures comprise: 3:1 wt. mixtures of sodium carbonate and calcium carbonate having a 5 micron particle diameter; 2.7:1 wt. mixtures of sodium sesquicarbonate and calcium carbonate having a particle diameter of 0.5 microns; 20:1 wt. mixtures of sodium sesquicarbonate and calcium hydroxide having a particle diameter of 0.01 micron; and a 3:3:1 wt. mixture of sodium carbonate, sodium aluminate and calcium oxide having a particle diameter of 5 microns.

A seeded builder comprising a mixture of sodium carbonate and calcium carbonate is especially preferred herein. A highly preferred seeded builder comprises a 30:1 to 5:1 (wt. $Na_2CO_3:CaCO_3$) mixture of sodium carbonate and calcium carbonate wherein the calcium carbonate has an average particle diameter from 0.01 micron to 5 microns.

The complex aluminosilicates, i.e., zeolite-type materials, are another useful type of detergency builder in the present process and compositions, since these materials readily soften water, i.e., remove $Ca++$ hardness. Both the naturally-occurring and synthetic "zeolites," especially the zeolite A and hydrated zeolite A materials, are useful for this builder/softener purpose. A description of zeolite A materials and a method of preparation appears in U.S. Pat. No. 2,882,243, entitled MOLECULAR SIEVE ADSORBENTS, issued Apr. 14, 1959, incorporated herein by reference.

The aqueous crutcher mixes used in the present process can also contain all manner of detergency adjunct materials and carriers commonly found in laundering and cleaning compositions. For example, various perfumes, optical bleaches, fillers, anti-caking agents, fabric softeners and the like can be present to provide the usual benefits occasioned by the use of such materials in detergent compositions.

Perborate bleaches commonly employed in European detergent compositions can also be present as a component of detergent compositions prepared in the present manner, and are added thereto as dry admixes.

Enzymes, especially the thermally stable proteolytic and lipolytic enzymes used in laundry detergents, can be dry-mixed in the compositions prepared herein.

As can be seen from the foregoing, soap and non-soap detergent compositions prepared in the manner of this invention can contain all manner of commonly-used ingredients typically employed in fully-formulated, free-flowing, powdered, flaked and granular cleansing compositions and toilet bars. Compositions which contain any of the phosphate-based, nitrilotriacetate-based or zeolite-based builders are especially preferred for detergency use and are readily prepared in the manner of this invention. The Peterson process drying agent soaps can be used to adjust the moisture content of such compositions to any desired level, depending on the intended end use of the finished product.

The process of this invention is carried out by preparing an aqueous crutcher mix comprising water, a wet soap or non-soap synthetic detersive surfactant, optional builders and auxiliary agents, etc., according to the desires of the formulator. The mixture is slurried until homogeneous. The Peterson process drying agent soap is added to the mix in a quantity sufficient to adjust the total moisture content to the desired level. It will be appreciated that the process herein can be carried out using conventional apparatus used in the detergent industry.

The following examples illustrate the practice of this invention but are not intended to be limiting thereof.

EXAMPLE I

Preparation of Substantially Anhydrous Sodium Soap

To a mixture of 50 g. (0.067 mole) of a 50:50 mixture of tallow and coconut fats in 250 mls. of substantially anhydrous acetonitrile at a temperature of 75° C., was added 8.15 g. (0.20 mole) of finely powdered 98% sodium hydroxide, according to the Peterson process. The reaction was exothermic and refluxed vigorously, without extraneous heating, about 2 minutes after the addition of the sodium hydroxide. The reaction mixture was stirred at reflux temperature for a total of 5 minutes. During this time, a layer of fine, white, powdered sodium soap formed in the reaction vessel.

The solid soap was collected by filtration and air dried overnight to remove entrained acetonitrile. The sodium soap prepared in this manner is substantially anhydrous and is ready for use as a drying agent in the present process.

In the process of Example I, the solid NaOH is replaced by an equivalent amount of powdered LiOH.H$_2$O, KOH, RbOH and CsOH, respectively, and substantially dry soaps suitable for use as drying agents are secured.

EXAMPLE II

Preparation of Potassium Myristate

To a solution of 12.2 g. (0.05 mole) of methyl myristate in 120 mls. of acetonitrile was added 3.3 g. (0.05 mole) of finely pulverized 85% (15% entrained moisture) potassium hydroxide, according to the Peterson process. The reaction mixture was stirred at substantially room temperature and monitored by following the rate of disappearance of methyl myristate by gas phase chromatographic analysis. After 6 hours, methyl myristate was no longer detectable. The precipitated sodium myristate was isolated by vacuum filtration and air dried overnight to remove solvent. The substantially water-free (ca. 5% H$_2$O) potassium myristate prepared in this manner is suitable for use as a drying agent in the present process.

In the process of Example II, the acetonitrile is replaced with an equivalent amount of propionitrile and equivalent results are secured.

EXAMPLE III

Preparation of Partially Hydrated, Solid Sodium Soap

100 Pounds of decolorized, commercial grade mixed (50:50) coconut and palm oil triglycerides are dissolved in 40 gallons of acetonitrile. 34 Pounds of a 50% aqueous solution of sodium hydroxide are poured onto the acetonitrile solution and the mixture is stirred, with gentle heating, in a closed soap kettle fitted with a water-cooled reflux condenser. Sufficient external heat is applied to the kettle, intermittently, to maintain refluxing for a period of 1 hour. At the end of this time, the kettle is cooled and the solid soap product is recovered by filtration, washing with acetonitrile, and air drying.

The white, solid soap powder prepared in the foregoing manner contains ca. 7% by weight of water and is suitable for use as the drying agent soap in the manner of the present invention.

In the process of Example III, the concentrated NaOH solution is replaced by an equivalent amount of a concentrated aqueous solution of LiOH and a solid, filterable, lithium soap product suitable for use as a drying agent herein is secured.

In the process of Example III a concentrated aqueous solution of KOH is used in place of the NaOH solution. The resulting soap is tacky, excessively hydrated, and is not suitable for use as a drying agent in the manner of this invention.

EXAMPLE IV

Preparation of Bar Soap

A bar soap composition is prepared in the manner of this invention, as follows.

| Ingredient | Wt. % |
|---|---|
| Sodium soap* | 48 |
| Sodium soap** | 48 |
| Stearic acid | 1.5 |
| TiO$_2$ (opacifier) | 0.5 |
| Perfume and minors | Balance |

*Wet process soap comprising ca. 22% by weight water
**Anhydrous sodium soap prepared in the manner of Example I, herein The foregoing ingredients are admixed thoroughly in a standard soap-maker's plodder, extruded through a soap-maker's extruder and fashioned into toilet bars using standard equipment.

A toilet bar prepared in the foregoing manner is not "smeary" or tacky and is suitable for use without further drying.

In the composition of Example IV, the anhydrous sodium soap drying agent is replaced by an equivalent amount of the potassium myristate prepared in the manner of Example II, herein, and an excellent bar soap is secured without further drying.

EXAMPLE V

Preparation of Bar Soap

A complexion soap composition is prepared in the manner of this invention, as follows.

| Ingredient | Wt. % |
|---|---|
| Sodium soap* | 27 |
| Sodium soap** | 63 |
| Glycerine | 6 |
| Stearic acid | 2 |
| TiO$_2$ (opacifier) | 1 |
| Perfume and minors | 1 |

*Wet process soap comprising ca. 25% by weight water
**Sodium soap containing ca. 7% by weight water, prepared in the manner of Example III, herein.

Following standard practice, the foregoing ingredients are admixed thoroughly, extruded and fashioned into toilet bars using standard soap making equipment.

Bar soap prepared in the foregoing manner is not smeary or tacky and is suitable for use without further drying. The soap lathers well in both hard and soft water.

EXAMPLE VI

Laundry Detergent Composition

A laundry detergent composition is prepared in the manner of this invention, as follows.

A mixture comprising: 1 part by weight $C_{12-13\ (avg.)}$ alkyl benzene sulfonate, sodium salt; 1 part by weight sodium tripolyphosphate; 1 part by weight sodium sulfate; 0.1 part by weight minors; and 5 parts by weight water is mixed thoroughly in a soap crutcher. After a homogeneous slurry is secured, the substantially anhydrous sodium soap drying agent (prepared in the manner of Example I, herein) is added to the crutcher mix in powder form (ca. 500-1500 micron) and blended thoroughly therewith. Sufficient anhydrous soap is added to adjust the water content to ca. 10%–12% by weight of the total crutcher mix. The soap absorbs the water in the crutcher mix to provide a mass having a substantially dry "feel" and appearance. The mass is granulated with conventional equipment to a homogeneous detergent composition which is suitable for use in fabric laundering operations without further drying.

EXAMPLE VII

Laundry Detergent Composition

A laundry detergent composition is prepared in the manner of this invention, as follows.

A mixture comprising: 1 part by weight $C_{11.8}$ LAS, sodium salt; 1 part by weight sodium nitrilotriacetate; 1 part by weight sodium sulfate; 0.5 part by weight Kyro EOB commercial nonionic surfactant; 0.1 part by weight minors; and 5 parts by weight water is mixed thoroughly in a soap crutcher. After a homogeneous slurry is secured, the substantially anhydrous sodium soap drying agent (prepared in the manner of Example I, herein) is added to the crutcher mix in powder form (ca. 500-1500 micron) and blended thoroughly therewith. Sufficient anhydrous soap is added to adjust the water content to ca. 6%–8% by weight of the total crutcher mix. The soap absorbs the water in the crutcher mix to provide a mass having a substantially dry "feel" and appearance. The mass is granulated with standard equipment to a homogeneous detergent composition which is suitable for use in fabric laundering operations without further drying.

The foregoing procedure is modified by adjusting the water content of the crutcher mix to ca. 13% using the dry soap of Example I. The resulting composition is especially adapted to being compacted into laundry detergent tablets.

In the composition of Example VII, the sodium nitrilotriacetate builder is replaced by an equivalent amount of hydrated Zeolite A (1-10 micron particle size range) as the builder and water softening ingredient and equivalent results are secured.

What is claimed is:

1. An energy-saving process for adjusting the water content of wet soaps, wet non-soap detersive surfactants, or wet crutcher mixes to a lower total water content by adding thereto a quantity of a drying agent which comprises a soap having a low water content which is prepared by saponifying carboxylic acid esters with alkali metal hydroxides in a reaction medium which comprises an alkyl nitrile.

2. A process according to claim 1 wherein the wet soap has a water content of greater than about 14%, by weight.

3. A process according to claim 2 wherein the drying agent soap has a water content in the range from about 0% to about 14%, by weight.

4. A process according to claim 3 wherein the drying agent soap is prepared by saponifying a $C_{10}$–$C_{20}$ fatty acid ester or glyceride, or mixture thereof, with an alkali metal hydroxide which is a member selected from the group consisting of lithium hydroxide, sodium hydroxide, and potassium hydroxide.

5. A process according to claim 4 wherein the glyceride comprises the mixed glyceride esters derived from animal fats and oils or vegetable fats and oils.

6. A process according to claim 5 wherein the alkyl nitrile is acetonitrile.

7. A process according to claim 1 wherein the wet non-soap detersive surfactant has a water content greater than about 14%, by weight.

8. A process according to claim 7 wherein the non-soap detersive surfactant is an anionic surfactant.

9. A process according to claim 8 wherein the non-soap anionic detersive surfactant is a water-soluble alkyl benzene sulfate or sulfonate.

10. A process according to claim 9 wherein the drying agent soap has a water content in the range from about 0% to about 14%, by weight.

11. A process according to claim 10 wherein the drying agent soap is prepared by saponifying a $C_{10}$–$C_{20}$ fatty acid glyceride, or mixture thereof, with an alkali metal hydroxide which is a member selected from the group consisting of lithium hydroxide, sodium hydroxide, and potassium hydroxide.

12. A process according to claim 11 wherein the glyceride comprises the mixed glyceride esters derived from animal fats and oils or vegetable fats and oils.

13. A process according to claim 12 wherein the alkyl nitrile is acetonitrile.

14. A process according to claim 1 wherein the wet crutcher mix comprises a wet soap or a wet non-soap detersive surfactant and auxiliary detersive agents and has a moisture content greater than about 14%, by weight.

15. A process according to claim 14 wherein the auxiliary detersive agents are detergency builders.

16. A process according to claim 15 wherein the builders are selected from the group consisting of phosphate-based builders, nitrilotriacetate-based builders and zeolite-based builders.

17. A process according to claim 16 wherein the non-soap detersive surfactant is a sulfated or sulfonated organic detersive surfactant.

18. A composition of matter prepared in the manner of claim 1.

* * * * *